United States Patent
Nandi et al.

(10) Patent No.: US 11,311,518 B1
(45) Date of Patent: Apr. 26, 2022

(54) PARENTERAL DOSAGE FORM OF β3 ADRENORECEPTOR AGONISTS

(71) Applicant: Jubilant Pharma Holdings Inc., Yardley, PA (US)

(72) Inventors: Indranil Nandi, Yardley, PA (US); Tusharmouli Mukherjee, Yardley, PA (US); Nagabasayya R Chikkamath, Noida (IN)

(73) Assignee: Jubilant Pharma Holdings Inc., Yardley, PA (US)

( * ) Notice: Subject to any disclaimer, the term of this patent is extended or adjusted under 35 U.S.C. 154(b) by 0 days.

(21) Appl. No.: 17/396,638

(22) Filed: Aug. 6, 2021

Related U.S. Application Data

(60) Provisional application No. 63/216,275, filed on Jun. 29, 2021.

(51) Int. Cl.
| | |
|---|---|
| *A61K 31/426* | (2006.01) |
| *A61K 47/26* | (2006.01) |
| *A61K 47/02* | (2006.01) |
| *A61K 47/12* | (2006.01) |
| *A61K 9/00* | (2006.01) |

(52) U.S. Cl.
CPC .......... *A61K 31/426* (2013.01); *A61K 9/0019* (2013.01); *A61K 47/02* (2013.01); *A61K 47/12* (2013.01); *A61K 47/26* (2013.01)

(58) Field of Classification Search
CPC ............................ A61K 31/426; A61K 31/427
See application file for complete search history.

(56) References Cited

U.S. PATENT DOCUMENTS

2018/0036288 A1\* 2/2018 Takae ..................... A61K 47/50

OTHER PUBLICATIONS

Nazar (Colloid and Polymer Science vol. 298 pp. 263-271 published Jan. 24, 2020) (Year: 2020).\*
Hao (Journal of Pharmacology and Experimental Therapeutics vol. 369 pp. 419-427. Published 2019) (Year: 2019).\*
Kasashima (Chem. Pharm. Bull vol. 64 pp. 1304-1309. Published 2016). (Year: 2016).\*
Nazar (Colloid and Polymer Science vol. 298 pp. 263-271 (2020). (Year: 2020).\*

\* cited by examiner

*Primary Examiner* — Theodore R. Howell
*Assistant Examiner* — George W Kosturko
(74) *Attorney, Agent, or Firm* — William D. Hare, Esq.; McNeely, Hare & War, LLP

(57) ABSTRACT

Disclosed are the injection compositions of β3 adrenoreceptor agonists such as mirabegron or their pharmaceutically acceptable salts or solvates or esters thereof. The present invention also relates to methods for preparing injection compositions and methods of using these dosage forms for the treatment of obesity, other related metabolic diseases, and reduction/removal of fat. The injection compositions as per the present invention have advantages of simple preparation, simple and convenient application, easy absorption, and better effect of treating. The compositions can also be used in cases where oral administration of the drug is not possible due to underlying conditions or concerns around inadequate oral absorption. The injection compositions as per the present invention have desirable pharmaceutical technical attributes.

14 Claims, No Drawings ered States Patent

PARENTERAL DOSAGE FORM OF β3 ADRENORECEPTOR AGONISTS

FIELD OF THE INVENTION

The present invention relates to parenteral dosage forms of β3 adrenoreceptor agonists or their pharmaceutically acceptable salts or solvates or esters thereof such as mirabegron. The present invention also relates to pharmaceutical compositions (e.g., lyophilized and/or aqueous compositions) comprising β3 adrenoreceptor agonists, methods for preparing these parenteral dosage forms, and methods of use thereof.

BACKGROUND OF THE INVENTION

Mirabegron is one of the β3-adrenergic receptor agonist approved for the treatment of overactive bladder and its associated symptoms. Mirabegron is chemically known as (R)-2-(2-aminothiazol-4-yl)-4'-{2-[(2-hydroxy-2 phenylethyl)amino]ethyl}acetanilide. It is represented with the following chemical structure:

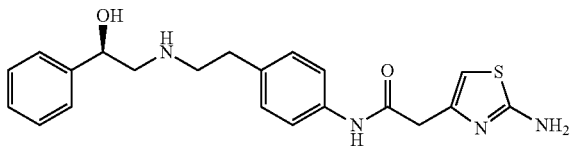 [SMILES: Nc1nc(CC(=O)Nc2ccc(CCNC[C@H](O)c3ccccc3)cc2)cs1]

Presently, mirabegron is approved in the form of solid oral dosage forms in the US market as extended-release tablets in strengths of 25 mg and 50 mg. Mirabegron compound is disclosed in U.S. Pat. No. 6,346,532.

U.S. Pat. No. 10,842,780 disclose sustained-release, hydrogel-forming oral formulations of mirabegron. U.S. Pat. No. 8,835,474, RE44,872 disclose methods of using mirabegron for the treatment of overactive bladder (OAB). U.S. Pat. No. 8,772,315 disclose combinations of mirabegron and solifenacin and methods of using such combinations for the treatment of OAB.

The use of β3-adrenergic receptor agonists including mirabegron in the treatment of obesity, metabolic disease, and reducing fat accumulation is known in the literature. Effect of mirabegron to stimulate the activity of brown adipose tissue (BAT) thermogenesis was recently disclosed in 2015 (Cypess et al., "Activation of human brown adipose tissue by a beta3-adrenergic receptor agonist," *Cell metabolism* 21:33-38 (2015)). U.S. Patent Publication No. 2018/0326080 discloses the utilization of novel polymer-based systems that allow controlled generation of brown/beige adipose tissues for the treatment of obesity and diabetes. This publication also discloses making a microsphere polymer-based drug delivery system via combining a drug with a polymer matrix system.

However, till date, no β3-adrenergic receptor agonist is approved in the USA market for the treatment of obesity and its related metabolic disorders and/or fat removal or reduction. Moreover, the determination of critical parameters of various clinical candidates or molecules associated with drug development essentially requires successful optimization of technical parameters like the selection of suitable dose, suitable dosage form, suitable route of administration, suitable dosing regimen, effect in animals, and humans.

In the pharmaceutical industry, there is a constant need to work on identifying and developing novel pharmaceutical compositions that certainly affect the drug's dissolution profile, bioavailability, bioequivalence, stability, etc. These factors all play important roles in achieving the desired therapeutic effect, and successful dosage form development with desired technical attributes. Therefore, in the case of mirabegron too, there is an unmet need to develop parenteral pharmaceutical compositions with desirable technical attributes such as solubility, drug release, stability, bioavailability, and patient compliance.

Thus, there is an unmet need to provide an effective drug delivery system of an β3-adrenergic receptor agonist, such as mirabegron for the treatment of obesity, reduction of localized fat, and/or related metabolic disorders and methods for making such delivery systems.

SUMMARY OF THE INVENTION

The present invention relates to novel parenteral compositions of β3-adrenergic receptor agonists and processes for preparing such compositions.

The present invention relates to novel injection compositions of mirabegron and processes for preparing such compositions.

The present invention relates to pharmaceutical compositions (e.g., lyophilized and/or aqueous compositions) comprising mirabegron and methods of use thereof.

The present invention also relates to injection compositions comprising mirabegron and at least one or more pharmaceutically acceptable excipients selected from the group consisting of solvents, co-solvents, solubilizing agents, surfactant or wetting agents, permeation enhancers, tonicity adjusting agents, stabilizers, pH adjusting agents, buffering agents, carriers, diluents, suspending agents, complexing agents, preservatives, antioxidants, surface modifiers and combination thereof.

The present invention also relates to the use of the therapeutically effective amount of injection compositions of mirabegron in the manufacture of a medicament for treating obesity, and its related metabolic disorders, reduction/removal of localized fat, hypertension, patients at risk of having diabetes (pre-diabetes), diabetes, cardiovascular diseases, hyperglycemia, gallbladder diseases, excess fat on the chin (submental fullness or double chin disorder), binge eating, hypothyroidism, excess fat on the breast, adiposis dolorosa, benign symmetric lipomatosis, lipedema, familial lipodystrophy, familial partial lipodystrophy, HIV lipodystrophy, Bardet-Biedl syndrome, hypertrophy of dorsocervical fat/dorsocervical fat hypertrophy ("buffalo hump"), lipoma, lipomatosis, moon facies, Down syndrome, pseudo-Cushing syndrome, Cohen syndrome, Cushing syndrome, Prader-Willi syndrome, Turner syndrome, or Madelung disease and even some types of cancer.

The details of one or more embodiments of the present invention are outlined in the description below. Other features, objects, and advantages of the invention will be apparent from the description.

DETAILED DESCRIPTION

As used herein, the term "β3-adrenergic receptor agonist", "β3-adrenoreceptor agonists" or "beta-3 adrenergic receptor agonist" includes compounds such as mirabegron, vibegron, solabegron. Preferably, the compound is mirabegron. "Mirabegron" is used in a broad sense to include not only mirabegron per se (free base) but also its pharmaceutically acceptable salts, solvates, esters, hydrates, enantiomers, derivatives, isomers, stereoisomers, diastereomers, metabolites, polymorphs, and prodrugs thereof. Polymorph may refer to various crystalline and amorphous forms of mirabegron.

As used herein, the term "composition", "formulation", "dosage form" as in pharmaceutical composition, is intended to encompass a drug product comprising mirabegron, and other inert ingredient(s) (pharmaceutically acceptable excipients). Such pharmaceutical compositions are synonymous with "formulation", "injectable composition", "injection composition", "parenteral composition", and "dosage form" and are used synonymously throughout the application.

The term "parenteral" or "injection" or "injectable" as used herein refers to routes selected from subcutaneous (SC), intravenous (IV), intramuscular (IM), intradermal (ID), intraperitoneal (IP), depot injection, or via an implantable pump, and the like. Transcutaneous is also contemplated as a route of delivery for the pharmaceutical compositions as per present invention. The formulations according to an aspect of the application may be in the form of lyophilized powders, liquid concentrates, ready-to-dilute, and/or ready-to-use solutions. The term "ready-to-dilute" refers to any preparation which is ready for dilution using water, water for injection, dextrose solution, saline solution, or any other infusion medium for administration to the patient. The term "ready-to-use" refers to any preparation which is ready to be administered to the patient directly without any further dilution or processing.

Injection or parenteral as per the present invention can be injected into the abdomen, chin, waist, arms, legs, knees, thigh, chest, breast, neck, face, buttocks, lateral buttock, peri-orbital region, intra-orbital region, or to a particular fat deposit area. The term "overweight", as used herein, refers to an adult individual having a body mass index (BMI) greater than or equal to 24 and less than 27. The term "obese", as used herein, refers to an adult individual having a body mass index (BMI) of greater than or equal to 30.

The compositions as per the present invention include injection preparations, such as liquid dosage forms (liquids, liquid dispersions, solutions, suspensions, emulsions), gels, colloids, dry powder, implants, biodegradable or non-biodegradable microparticles/microspheres, lyophilized formulations, and mixed immediate release and controlled release formulations. Preferably, the composition is an aqueous-based immediate-release injection dosage form.

As used herein, the pharmaceutically acceptable salt(s) include, but are not limited to, maleic, citric, gluconic, lactic, malic, mandelic, cinnamic, citraconic, aspartic, stearic, palmitic, itaconic, glycolic, p-aminobenzoic, glutamic, benzene sulfonic, theophylline acetic acids, fumaric, benzoic, ascorbic, embonic, succinic, oxalic, bismethylenesalicylic, methanesulfonic, ethanedisulfonic, acetic, propionic, tartaric, salicylic, 8-halotheophyllines (e.g. 8-bromo-theophylline), hydrochloric, hydrobromic, sulfuric, sulfamic, phosphoric and nitric acids and the like.

The term "patient" and/or "subject" are used interchangeably herein. In some embodiments, the patient or subject is a human. In further embodiments, the patient or subject is an animal. In some embodiments, the human can be of any age such as adult, adolescent, pediatric or geriatric. As used herein, the term "therapeutic agent" means an agent utilized to treat, combat, ameliorate, prevent or improve an unwanted condition or allergy, or disease of a patient.

The term "therapeutically effective amount" is such that when administered, the pharmaceutical composition of the present invention provides desired therapeutic effect in the treatment of diseases as described herein. The dosage administered to a patient can be as single or multiple doses depending upon a variety of factors, including the drug's administered pharmacokinetic properties, the route of administration, patient conditions and characteristics (sex, age, body weight, health, size, etc.), and extent of symptoms, concurrent treatments, frequency of treatment and the effect desired.

"Substantially" as used herein refers to the pharmaceutical composition, which comprises less than 1% or less than 0.5% of a particular component or excipient as described herein.

The term "excipient" means one or more pharmacologically inactive components comprising one or more of solvents, co-solvents, solubilizing agents, surfactant or wetting agents, permeation enhancers, tonicity adjusting agents, stabilizers, pH adjusting agents, buffering agents, carriers, diluents, suspending agents, complexing agents, preservatives, antioxidants, surface modifiers and combination thereof.

Unless otherwise stated the weight percentages expressed herein are based on the final weight or volume of the composition or formulation. As used herein, the term "about" means ±approximately 20% of the indicated value, such that "about 10 percent" indicates approximately 08 to 12 percent.

The term "stable" refers to any preparation of mirabegron having sufficient stability to allow storage at a convenient temperature, such as between about 0° C. and about 60° C., for a pharmaceutically acceptable duration of time, preferable at 40° C. and 75% relative humidity (R.H.) or at 25° C. and 60% R.H. Preferably, the compositions are stable for a period of time, such as at least about one week, at least about one month, at least about three months, at least about six months, at least about one year, or at least about 2 years. The purity of mirabegron in compositions as per the present invention ranges from at least 99.99%, 99%, 98%, 97%, 96%, or 95%.

Mirabegron is practically insoluble in water. Moreover, the bioavailability of mirabegron is affected by the presence of food in the GI (Gastro-Intestinal) tract. Therefore, to prevent this food effect, the commercially available pharmaceutical formulations of mirabegron are in the form of extended-release tablet formulation based on an orally controlled absorption system (OCAS®) technology. These properties of mirabegron may pose multiple challenges for formulation scientists in the dosage forms development. Moreover, the use of oral dosage form in the treatment of obesity and its related metabolic disorders may not be a suitable approach due to the number of factors such as frequent dosage administration, long treatment period, patient compliance, and low bioavailability.

The bioavailability of the β3-adrenergic receptor agonists such as mirabegron can be improved via the injectable/parenteral route of administration and may provide a higher level of bioavailability than the oral route. The increase in bioavailability of an injectable formulation can provide therapeutic plasma concentration levels with a dose that can be administered. However, the development of injection dosage forms such as aqueous-based injection is not feasible due to the very poor solubility of the drug in water. Further, formulation development of injectable dosage form is highly challenging. The stability of the drug in the final injection product is a primary concern to the formulation scientist. The drug substances are less stable in aqueous media than solid dosage forms, and it is very important to properly stabilize and preserve liquid aqueous formulations such as injectable solutions. Acid-base reactions, acid or base catalysis, oxidation, and reduction can occur in these products. These reactions can arise from drug substance-ingredient interactions, ingredient-ingredient interactions, or container-product interactions. For pH-sensitive compounds, any of these interactions may alter the pH and may cause precipitation. In addition to stabilization of pharmaceutical preparations against chemical and physical degradation, multiple dosage unit preparations must usually be protected against microbial contamination. In contrast to solid preparations, aqueous solutions often provide excellent growth media for microorganisms such as molds, yeast, and bacteria. Contamination by these microorganisms may occur during the manufacturing or when a dose is taken from multiple dosage unit formulations. The growth of the microorganisms occurs when a sufficient amount of water is present in the formulation. The inventors of the present invention developed compositions that overcome all challenges and exhibits many desired formulation technical attributes required for injection compositions.

The pharmaceutical compositions of the present invention comprise mirabegron from about 0.005 µg to 500 mg per day. In some embodiments, the dose of mirabegron ranges from about 0.05 µg to about 200 mg per day, about 0.05 µg to about 100 mg per day, about 0.05 µg to about 50 mg per day, about 0.05 µg to about 60 mg per day, about 0.05 µg to about 40 mg per day, about 0.05 µg to about 30 mg per day, about 0.05 µg to about 20 mg per day, about 0.05 µg to about 10 mg per day, about 0.05 µg to about 5 mg per day, 0.05 µg to about 2 mg per day, about 0.05 µg to about 1 mg per day, and about 0.05 µg to about 0.5 mg per day.

The present invention relates to pharmaceutical compositions (e.g., lyophilized and/or aqueous compositions) comprising β3-adrenergic receptor agonists such as mirabegron and methods of use thereof.

The present invention relates to the injection composition of β3-adrenergic receptor agonists and at least one or more pharmaceutically acceptable excipients and processes for preparing such compositions.

The compositions can be lyophilized (e.g., as a powder) for long-term storage. The lyophilized formulations can be reconstituted as biocompatible formulations for administration to a subject in need thereof. In certain non-limiting embodiments, the composition is formulated as a liquid. In certain non-limiting embodiments, the composition is formulated as a clear liquid. Preferably, the composition is an aqueous solution.

In one embodiment, the present invention provides an injection composition comprising mirabegron and at least one or more pharmaceutically acceptable excipients and processes for preparing such compositions.

In another embodiment of the invention, there is provided an injection composition comprising at least: a) mirabegron, and b) a pharmaceutically acceptable carrier.

In another embodiment, the present invention also relates to injection compositions comprising mirabegron and at least one or more pharmaceutically acceptable excipients selected from the group consisting of solvents, co-solvents, solubilizing agents, surfactant or wetting agents, permeation enhancers, tonicity adjusting agents, stabilizers, pH adjusting agents, buffering agents, carriers, diluents, suspending agents, complexing agents, preservatives, antioxidants, surface modifiers, and combination thereof.

In another embodiment, the present invention further relates to an injectable composition of mirabegron, dispersed in an aqueous liquid vehicle.

In another embodiment of the invention, there is provided a liquid pharmaceutical composition suitable for parenteral administration comprising: a) mirabegron, b) one or more pH adjusting agents, and c) one or more parenteral solvents.

In another embodiment of the invention, the injection composition comprising: a) mirabegron, b) one or more pH adjusting agents, c) wetting agent, and d) one or more parenteral solvents.

In another embodiment of the invention, the injection composition comprising: a) mirabegron, b) one or more pH adjusting agents, c) wetting agent, and d) one or more parenteral solvents; wherein the pH of the composition is about 3.0 to about 7.0.

In another embodiment of the invention, the injection composition comprising: a) mirabegron, b) one or more pH adjusting agents, c) wetting agent, d) tonicity adjusting agent, and e) one or more parenteral solvents.

In another embodiment of the invention, the pH of the composition is about 2.0 to about 8.0. In another embodiment of the invention, the present disclosure provides a pharmaceutical composition, comprising: mirabegron, one or more pH adjusting agents, and water; wherein the pH of the composition is about 2.0 to about 7.0. Preferably, the pH is between about 3.0 and about 7.0. More preferably, the pH is between about 3.0 and about 5.5.

In some embodiments, the pH adjusting agent is selected from the group consisting of inorganic acids, organic acids, inorganic bases, and organic bases, borate buffers, acetate buffers, tartrate buffers, lactate buffers, citrate buffers, phosphate buffers, citric acid/phosphate buffers, carbonate/carbonic acid buffers, succinate/succinic acid buffers, ammonium buffers and combinations thereof. In another non-limiting embodiment, the pH adjusting agent is sodium acetate, sodium phosphate, sodium citrate, citric acid, L-arginine, glacial acetic acid, hydrochloric acid, or tromethamine.

In some embodiments, one or more wetting agents or surfactants or solubility enhancers or permeation enhancers are selected from the group consisting of one or more of anionic, cationic, non-ionic, or zwitterionic surfactants or mixtures thereof. In certain non-limiting embodiments, one or more wetting agents or surfactants or solubility enhancers or permeation enhancers are sodium lauryl sulphate, polysorbate, poloxamer, or any combination or mixture thereof. In certain non-limiting embodiments, the non-ionic surfactant is one or more polysorbate surfactant selected from the group consisting of polysorbate 20, polysorbate 40, polysorbate 60, polysorbate 80, and mixtures thereof.

In some embodiments, solvent is selected from ethanol, isopropanol, dimethyl sulfoxide, dimethylformamide, dimethylacetamide, glycerol, water, and mixtures thereof. In certain non-limiting embodiments, the solvent is water or a mixture of alcohol and water.

In some embodiments, a tonicity adjusting agent is selected from the group consisting of, sodium acetate, sodium chloride, dextrose, sodium lactate, calcium chloride, sodium bicarbonate, and potassium chloride, and/or any combination thereof.

In a further embodiment, the composition has an osmolality that is in the range from 100 to 600 mOsm/kg. In a further embodiment, the composition has an osmolality that is in the range from 100 to 500 mOsm/kg. In a further embodiment, the composition has an osmolality that is in the range from 100 to 400 mOsm/kg. In a further embodiment, the composition has an osmolality equal to and/or less than 350 mOsm/kg.

In a further embodiment, the water content of the composition is at least 10 weight (wt.) percent (%) more preferably at least 40 wt. %, still more preferably at least 60 wt.

%, yet more preferably at least 80 wt. %, most preferably at least 85 wt. %, and in particular at least 90 wt. %, based on the total weight of the composition. Besides water, the composition according to the invention may contain further solvents.

In another preferred embodiment, the present invention provides a pharmaceutical composition comprising mirabegron at concentrations about 0.001 mg/mL to about 200 mg/mL. Typically, the concentrations of mirabegron are in the range of about 10 mg/mL to about 100 mg/mL. In some embodiments, the mirabegron is present at a concentration of about 50.0 mg/mL. In other embodiments, the mirabegron is present at a concentration of about 25.0 mg/mL. In other embodiments, the mirabegron is present at a concentration of about 10.0 mg/mL. In other embodiments, the mirabegron is present at a concentration of about 5.0 mg/mL. In other embodiments, the mirabegron is present at a concentration of about 1.0 mg/mL or even less.

In another embodiment of the invention, the mirabegron injection composition is substantially free or free from preservatives and/or antioxidants. In certain non-limiting embodiments, the mirabegron injection composition is substantially free or free from alcohol-based preservatives. In another embodiment of the invention, the injection composition of mirabegron is substantially free or free from any alcohol-based excipients.

In another embodiment, the compositions of the present invention are free from propylene glycol.

In another embodiment, the compositions of the present invention are free from poly (lactic acid-co-glycolic acid) (PLGA).

In an embodiment, the amount of mirabegron in the composition of the present invention is from about 0.0001% to about 90% of the total injection composition. In a preferred embodiment, the amount of mirabegron in the composition of the present invention is about 0.001% to about 50% of the total composition. In a preferred embodiment, the amount of mirabegron in the composition of the present invention is about 0.001% to about 35% of the total composition. Preferably, from about 0.001% to about 20% of the total composition.

In another embodiment of the invention, there is provided an injection composition comprising: a) about 0.001% to about 90% of mirabegron, b) about 10% to about 99% of a pharmaceutically acceptable parenteral solvent, and c) at least one or more other pharmaceutically acceptable excipients.

In another embodiment of the invention, there is provided a liquid pharmaceutical composition suitable for parenteral administration comprising: a) about 0.001% to about 90% of mirabegron, b) about 0.01% to about 80% of one or more pH adjusting agents, and c) one or more parenteral solvents.

In another embodiment of the invention, there is provided a liquid pharmaceutical composition suitable for parenteral administration comprising: a) about 0.001% to about 90% of mirabegron, b) about 0.01% to about 80% of one or more pH adjusting agents, and c) from 0 to about 30% of one or more wetting agents, d) from 0 to about 30% of one or more tonicity adjusting agents, e) from 0 to about 20% of one or more preservatives, f) from 0 to about 20% of one or more antioxidants, and g) one or more parenteral solvents.

In another embodiment of the invention, there is provided a liquid pharmaceutical composition suitable for parenteral administration comprising: a) about 0.001% to about 20% of mirabegron, b) about 0.01% to about 20% of one or more pH adjusting agents, c) from 0.001% to about 10% of one or more wetting agents, d) from 0.001% to about 10% of one or more tonicity adjusting agents, and e) one or more parenteral solvents.

In another embodiment of the invention, there is provided a liquid pharmaceutical composition suitable for parenteral administration comprising: a) about 0.001% to about 10% of mirabegron, b) about 0.01% to about 5% of one or more pH adjusting agents, c) from 0.001% to about 1% of one or more wetting agents, d) from 0.001% to about 2% of one or more tonicity adjusting agents, and e) one or more parenteral solvents.

In another embodiment of the invention, there is provided a liquid pharmaceutical composition suitable for parenteral administration comprising: a) about 0.001% to about 20% of mirabegron, b) about 0.01% to about 20% of one or more pH adjusting agents selected from the group consisting of sodium phosphate, citric acid, sodium citrate, glacial acetic acid, hydrochloric acid, and c) from 0.001% to about 10% of one or more wetting agents selected from the group consisting of sodium lauryl sulphate, polysorbate, and poloxamer, d) from 0.001% to about 10% of one or more tonicity adjusting agents selected from the group consisting of, sodium acetate, sodium chloride, dextrose, sodium lactate, calcium chloride, sodium bicarbonate, potassium chloride, and e) one or more parenteral solvents.

In another embodiment of the invention, there is provided a liquid pharmaceutical composition suitable for parenteral administration comprising mirabegron, sodium acetate, glacial acetic acid, polysorbate-80, and water for injection.

In another embodiment of the invention, the weight ratio of mirabegron to the said wetting agent is 10:0.001 to 0.001:10. Preferably, the weight ratio of mirabegron to the said wetting agent is 10:0.01 to 0.01:10. Preferably, the weight ratio of mirabegron to the said wetting agent is 10:1.

In another embodiment of the invention, the weight ratio of mirabegron to the said tonicity adjusting agent is 10:0.001 to 0.001:10. Preferably, the weight ratio of mirabegron to the said tonicity adjusting agents is 10:0.01 to 0.01:10.

In another embodiment of the invention, the pH adjusting agent is present in the composition in a concentration of about 0.001 mg/ml to about 50 mg/ml. Preferably, from about 0.01 mg/ml to about 20 mg/ml.

In another embodiment of the invention, the pharmaceutical composition comprises: mirabegron at a concentration of from about 10 mg/ml to about 50.0 mg/mL, polysorbate 80 at a concentration of about 0.01 to 5 mg/mL, one or more pH adjusting agents, and water; wherein the pH of the composition is about 3.0 to about 7.0. In a preferred embodiment, the pH of the composition is about 2.5 to about 6.5.

In another embodiment of the invention, the injection composition is prepared by conventional methods for preparation in the art, including but not limited to, mixing, freeze-drying, spray-drying method, solvent-volatilizing method, emulsion-solvent volatilization, sterile filtration, recrystallization followed by aseptic micronization, dry or wet milling followed by gamma or e-beam irradiation sterilization and atomizing-extracting method. Other formulation techniques are also contemplated within the scope of the present invention.

In another embodiment of the invention, the injection composition is prepared by dissolving or suspending the mirabegron in a pharmaceutically acceptable vehicle under sterile conditions. In a preferred embodiment, the vehicle is water for injection.

In another embodiment of the invention, the process of preparing injection composition is carried out under aseptic conditions, and when grinding, the temperature should not exceed 40° C.

In one embodiment, the method provided herein comprises mixing mirabegron with one or more wetting agents, and one or more additives, and then adding aqueous media, and stirring until a clear solution is obtained.

In one embodiment, the invention relates to a process for preparing an injection composition comprising: a) preparing a first sterile solution comprising one or more pharmaceutically acceptable excipients, b) preparing a second sterile solution comprising mirabegron, c) dispersing both solutions to form the final sterile composition.

In one embodiment, the invention relates to a process for preparing an injection composition comprising: a) dissolving the drug in a solvent, b) charging the drug solution in another suitable solvent, cooling below an appropriate temperature, and c) filtering the particles of the drug, thus obtaining sterile particles.

In one embodiment, the invention relates to a process for preparing an injection composition comprising: a) collecting the suitable vehicle (such as water for injection) in a suitable container; b) cooling the vehicle of step a) to a suitable temperature range (such as 20 to 25° C.); c) adding suitable excipients (such as a wetting agent, tonicity adjusting agent) with stirring for a suitable time to produce a clear solution; d) adding the drug to the solution of step c) with stirring for a suitable time; e) stirring the solution of step d) for a suitable time and adjusting the pH using one or more suitable pH adjusting agents; f) making the volume up to final batch size using water for injection; g) filtrating the solution of step f) using suitable filters (such as 0.2-micron size); h) filling the solution of step g) in appropriate size vials; i) stoppering the vials using rubber stoppers; j) capping the vials using suitable seals (such as aluminum flip-off seals).

In one embodiment, the process also includes the step of sterilization. In one non-limited embodiment, the process also includes the step of terminal sterilization. In one non-limited embodiment, the process includes the step of aseptic filtration.

In one embodiment, the invention relates to a process for preparing a parenteral pharmaceutical composition of mirabegron comprising: a) purging the mixture with inert gas and/or, b) filtering the mixture through a filter e.g. with a filter having an average pore size of not more than 0.5 µm and/or, c) filling the mixture into a suitable container, and d) autoclaving the mixture at elevated temperature and elevated pressure e.g. at 121° C. and 2 bar for at least 20 minutes or by aseptic filtration method.

In one embodiment, the process for preparing the liquid composition of the present invention is conducted in an atmosphere of inert gas to minimize oxidation of mirabegron. In addition, headspace oxygen and moisture from the sealable vessel have to be removed. This can be established by purging the sealable container with an inert gas. Such inert gasses are for example nitrogen, argon or helium, or mixtures thereof. The preferred inert gas is nitrogen.

In one embodiment, the present invention provides a method of administering injection composition locally, intramuscularly, intravenously, or subcutaneously as described in the present invention. In certain non-limiting embodiments, the composition as per the present invention is suitable for administration into adipose tissue of the said subject.

In another embodiment, the composition is a sterile composition.

In another embodiment, the composition is free of microbial content during storage.

In certain non-limiting embodiments, the composition is formulated at a pH of between about 1 and about 10, or between about 1 and about 8, or between about 1 and about 6, or between about 1 and about 4, or between about 1 and about 2. In other non-limiting embodiments, the composition is formulated at a pH of between about 2 and about 10, or between about 4 and about 8, or between about 3 and about 7. In a preferred non-limiting embodiment, the composition is formulated at a pH of between about 2.0 and about 6.0. In another embodiment, the pH of the composition may be in the range from pH 2 to pH 5.5 or from pH 2.5 to pH 5.5. Preferably, from about 3.0 and about 5.5.

The pH may be measured by placing a pH meter directly into the liquid formulation, such as a pH meter having been calibrated for the appropriate pH range with standard aqueous buffers. Persons skilled in the art will know of other methods, which may be used to measure pH. These ranges are for measurements made at room temperature (20 to 25° C.). A person skilled in the art will know that the pH meter reading will vary depending on the temperature.

In another embodiment, the impurities present in the compositions during stability studies were detected by high-performance liquid chromatography (HPLC) equipped with a suitable detector (such as UV) operating at a suitable wavelength. The amount of impurities was calculated on a normalized peak area response ("PAR") basis. As an acceptable limit demonstrating sufficient stability at the corresponding sampling point, the sum of peaks of all individual impurities in the invention compositions should not exceed 2% of the total PAR. The peak size of any individual impurity should not exceed 1% of the total PAR.

In another embodiment, the temperatures at which the compositions of the present invention are kept for routine storage, within the period of the pharmaceutical shelf-life of the composition, are preferably between 2° and 8° C. The compositions are preferably stored in tightly stoppered original containers, typically closed glass vials. Under such conditions, the expected shelf-life of the compositions of the present invention is at least 12 months.

In another embodiment the injection composition of mirabegron includes particle size of mirabegron Active Pharmaceutical Ingredient (API), having a particle size distribution such that $D_{90}$ is less than about 200 µm, $D_{50}$ is less than about 100 µm and $D_{10}$ is less than about 50 µm. Preferably, particle size distribution is $D_{90}$ is less than about 100 µm, $D_{50}$ is less than about 70 µm and $D_{10}$ is less than about 30 µm. Preferably, the average particle size is from about 2 microns to 100 microns. Preferably, the average particle size is less than about 3 microns. The particle size of mirabegron can be achieved by any well-known particle size reduction processes, such as sifting, milling, micronization, fluid energy milling, media milling, ball milling, homogenization, milled through the high-pressure homogenizer, air-jet milling, and the like. The particle size of mirabegron can be measured by suitable techniques such as Laser light scattering (e.g. Malvern Light Scattering), Dynamic light scattering method (Zetasizer equipment), Coulter counter, microscopy, photon correlation spectroscopy, and any other technique known in the art.

In another embodiment, the injection composition has a viscosity of about 0.5 poise to about 50 poise at a shear rate of 1/s at 25° C. In some embodiments, the composition has a viscosity of about 0.5 poise to about 10 poise at a shear rate of 10/s at 25° C. In some embodiments, the composition has a viscosity of about 0.5 poise to about 4 poise at 100/s shear rate at 25° C.

In another embodiment, the injection composition of mirabegron is stable for at least 1 month, 3 months, preferably for 6 months, more preferably for 12 months, and more preferably for 24 months when stored at room temperature and/or refrigerated conditions.

In another embodiment, the injection composition of mirabegron remains stable and does not degrade during sterilization conditions in a stoppered vial under nitrogen by heating with steam at 121° C. for at least 15 minutes.

In another embodiment, the injection composition of mirabegron is expected to exhibit desired formulation technical attributes such as particle size, ease of manufacturing, drug sterility, pH, viscosity, drug release, dosage regimen, stability, patient compliance, and commercially viable and other requirements also.

In further embodiments, the injection composition of mirabegron exhibits desired pharmaceutical technical attributes in following tests such as foreign and particulate matter test, sterility test, bacterial endotoxin test, and package integrity leak test for container-closure integrity.

In another embodiment, the injection composition of mirabegron as per the present invention provides quick drug release, effective blood drug level, better therapeutic effects, and low side-effects, and thus overcome the challenges of conventional oral dosage forms by providing good therapeutic efficacy.

The pharmaceutical composition of the present invention may optionally be sterilized using methods known to the artisan. In another embodiment the injection composition of mirabegron includes sterilization. Various sterilization procedure includes, but not limited to, heat sterilization, terminal steam sterilization, dry heat sterilization, moist heat sterilization, filtration, membrane sterilization, radiation or gamma sterilization and the like. In one embodiment, the sterilization is carried out in an autoclave at 121° C. for 15 minutes. It is beneficial that the presently claimed composition is stable during heat sterilization. In an alternate embodiment, after the sterilization injection composition is aseptically packed into the respective container. In alternate embodiments, the composition is terminally sterilized or prepared in strict sterile conditions.

The injection compositions of the present invention are expected to exhibit desired technical characteristics based on tests such as 1) pH: pH is measured by using a pH meter, 2) Sterility Test: It can be carried out by inoculation of a culture medium with the composition. If there is no evidence of microbial growth then the preparation being examined passes the test for sterility, 3) Leakage test: Leakage test is employed to test the package integrity. A leakage test can be done by a dye bath test. The test container is immersed in a dye bath. Vacuum and pressure are applied for some time. The container is removed from the dye bath and washed. The container is then inspected for the presence of dye either visually or utilizing UV spectroscopy, 4) Pyrogen test, 5) BET (Bacterial Endotoxin Test), 6) Content uniformity, 7) Viscosity, 8) Clarity, 9) Drug release, and 10) Stability.

In a preferred embodiment, the composition according to the invention is adapted for local administration. In this regard, local administration includes every administration of the composition to a site that is identical to the site of disorder and/or at least is located nearby. In particular, the local administration has the purpose of delivering mirabegron directly to the desired site of action, thereby avoiding systemic side effects.

In another preferred embodiment, the composition according to the invention is adapted for systemic administration. In this embodiment, the administration of the composition preferably has the purpose of inducing a systemic action of mirabegron.

In another embodiment, the injection composition of mirabegron is intended for use as a single dose. In another embodiment, the injection composition of mirabegron is intended for use in multiple doses.

In an embodiment, the composition as per the present invention is packed in a suitable container selected from a vial, ampoule, syringe, pen (single or multi-compartment), auto-injector, and cartridge. In certain non-limiting embodiments, the container includes, but is not limited to, glass vials (for example, but not limited to, flint glass vials), ampoules, plastic flexible containers, for example, but not limited to, PVC (polyvinyl chloride) containers, VisIV™ plastic containers, CR3 elastomer copolyester ether containers, CZ resin containers, polypropylene containers, and syringes.

According to another aspect of the present invention, the invention provides a pharmaceutical kit, wherein the composition comprising a drug and at least one excipient are contained in a first container, and the suitable solvent or diluent is contained in a second, separate container. Preferably, at least one of the first and second containers is a syringe, auto-injector, an ampoule, a vial, a pen, or a cartridge, either disposable or not, which can be single-use or multiple uses. In one aspect of the present invention, the composition is directed to a kit comprising a first container selected from the syringe, auto-injector, vial, ampoule, pen, or cartridge, containing at least one excipient and a drug in the appropriate amounts and a second container selected from the syringe, vial, ampoule, auto-injector, pen or cartridge comprising at least one excipient like solvents or diluents. When required, the contents of both containers are combined, for example through a connector or by using male-female syringes and mixed so that the compositions according to the invention are reconstituted, for example by moving forwards and backward the plungers of the syringes. Vial refers to any container of any shape or size, designed to hold the injection composition as per present invention.

In another embodiment of the invention, the present invention provides a method for reducing or non-surgical removal of body fat in an individual by administering mirabegron injection compositions.

In another embodiment, the present invention provides a method of administering injection composition described herein to a subject, e.g., a human or domesticated animal subject. In some embodiments, administration can occur at least daily, once in every three days, weekly, once in two weeks, once in three weeks, monthly, once in two months, once in three months, or once in six months.

The prefilled syringes or vials or ampoules or pens or cartridges or auto-injector as per present invention may contain volumes from about 10 ml or less, 9.5 ml or less, 9 ml or less, 8.5 ml or less, 8 ml or less, 7.5 ml, or less, 7 ml or less, 6.5 ml or less, 6 ml or less, 5.5 ml or less, 5 ml or less, 4.5 ml or less, 4 ml or less, 3.5 ml or less, 3 ml or less, 2.5 ml or less, 2 ml or less, 1.5 ml or less, 1 ml or less, 0.5 ml or less, 0.1 ml or less.

In another embodiment of the invention, there is provided a use of a therapeutic effective amount of injection composition of mirabegron in the manufacture of a medicament for treating overactive bladder, pediatric neurogenic detrusor overactivity (NDO), obesity, and its related metabolic disorders, reduction/removal of localized fat, hypertension, patients at risk of having diabetes (pre-diabetes), diabetes, cardiovascular diseases, hyperglycemia, gallbladder diseases, excess fat on the chin (submental fullness or double chin disorder), binge eating, hypothyroidism, excess fat on the breast, adiposis dolorosa, familial partial lipodystrophies (FPLD), benign symmetric lipomatosis, lipedema, familial lipodystrophy, familial partial lipodystrophy, HIV lipodystrophy, Bardet-Biedl syndrome, hypertrophy of dorsocervical fat/dorsocervical fat hypertrophy ("buffalo hump"), lipoma, lipomatosis, moon facies, Down syndrome, pseudo-Cushing syndrome, Cohen syndrome, Cushing syndrome, Prader-Willi syndrome, Turner syndrome, or Madelung disease.

In another embodiment of the invention, there is provided a use of a therapeutic effective amount of injection composition of mirabegron for treating a condition selected from the group comprising of double chin disorder, benign symmetric lipomatosis, adiposis dolorosa, lipedema, and familial partial lipodystrophy.

In an embodiment, the present invention provides pharmaceutical compositions and methods to reduce regional fat, adipose tissue, adipocyte, and regional or localized adiposity.

In one embodiment, the present invention provides a method of fat reduction by reducing the number of fat cells, the volume of fat cells as measured by at least one of volume, size, mass, bulk, density, amount, and/or quantity. The present invention is expected to reduce fat by greater than or equal to 80%, greater than or equal to 60%, greater than or equal to 50%, greater than or equal to 30%, greater than or equal to 20%, greater than or equal to 10%, or greater than or equal to 5%.

In an embodiment, the injection composition of mirabegron is administered into adipose tissue. In an embodiment, the injection composition locally reduces adipose tissue. In a further embodiment, the injection composition reduces submental adipose tissue. In an embodiment, the fat is reduced from a body part selected from the group consisting of the abdomen, chin, waist, arm, leg, knee, thigh, chest, breast, neck, face, buttock, lateral buttock, peri-orbital region, and/or intra-orbital region.

In another embodiment of the invention, there is provided a use of the therapeutic effective amount of injection composition for the reduction of submental fat (double chin) in a subject, said method comprising administering about 0.001 mg to about 100 mg of said mirabegron per square centimeter of the skin area over said submental fat.

In another embodiment of the invention, the pharmaceutical composition as per the present invention is administered within a plurality of treatment sessions. In a further embodiment, each treatment session is spaced by at least 1 day. In other embodiment, each treatment session is separated from another treatment session by at least 2 to 30 days. In another embodiment of the invention, a plurality of treatment sessions may include administration of injection composition up to a maximum of 80 injections.

In another embodiment of the invention, a plurality of treatment sessions by injection composition are spaced at least about 0.1 cm apart. In further embodiments, the plurality of treatment sessions by injection composition are spaced from about 0.1 cm to about 10 cm apart. In another embodiment, the plurality of treatment sessions by injection composition are spaced about 0.3 cm apart. In a further embodiment, space is usually measured by a marker to be applied to the affected area of the patient.

Experimental tests for the effect of mirabegron in reducing fat deposition in a subject in need thereof include, Pre-clinical studies including: 1) In-vitro tests (In Vitro Study of Mouse Preadipocyte Viability, Preadipocyte Differentiation, Preadipocyte Apoptosis, and Adipocyte Apoptosis), 2) Animal study (effect on inguinal lateral fat pad of hamsters/rats), 3) Clinical studies including: i) In vivo human study, ii) Body mass index (BMI) study (Quantitative methods for the analysis of weight loss or maintenance include measurements of body mass index (BMI). In some embodiments, BMI may be monitored by determining a subject's body mass and height and then dividing the individual's body mass by the square of their height, with the value given in units of kg/m. BMI values may range from underweight to obesity and may be used to assess how much a subject's body weight departs from what is normal or desirable for a person of his or her height.

In certain non-limiting embodiments, the injection formulations were evaluated to determine the effect of mirabegron in animals (such as C57BL/6 mice etc.). The purpose of this study was to determine the effect of mirabegron on modulation in biomarkers such as uncoupling protein 1 (UCP1), Peroxisome proliferator-activated receptor-gamma coactivator-1alpha (PGC-1α) and others in this category to check pharmacokinetics after single and multiple localized microinjections in iWAT (Inguinal white adipose tissue). Mirabegron at a dose up to 1 mg per animal has shown a statistically significant increase in expression of biomarkers in iWAT which clearly indicated that mirabegron is causing marked thermogenesis after localized microinjections.

Various useful solvent(s) or carrier(s) or vehicle(s) or parenteral solvent(s) include, but are not limited to, aqueous, non-aqueous solvents, oils, $C_2$-$C_6$ aliphatic alcohols, ethanol, 1-propanol, 2-propanol, 1-butanol, 2-butanol, 1-pentanol, 2-pentanol, 3-pentanol, isopropanol, benzyl alcohol, glycol ethers (e.g., including, but limited to, diethyleneglycol monoethyl ether (DGME, Transcutol®), butyl diglycol, dipropylene glycol n-butyl ether, ethyleneglycol monoethyl ether, dipropylene glycol monomethyl ether, propylene glycol monomethyl ether, propylene glycol monoethyl ether, liquid polyethylene glycols (PEGs) (PEG 200, PEG 300, PEG 400), carbonates (e.g., propylene carbonate), 2-pyrrolidone, N-methylpyrrolidone, dimethyl isosorbide, dimethylacetamide, glycerol formal, dichloromethane, chloroform, ethyl acetate, dioxane, ethyl ether, acetone, tetrahydrofuran, benzene, toluene, glacial acetic acid, tromethamine, L-arginine, petroleum ether, alkane, paraffine, dimethylsulfoxide, liquid polyethylene glycol, block copolymers of oxyethylene, polyoxyethylene alcohol, polyoxyethylene fatty acid esters, hydrocarbons, n-propane, n-butane, isobutane, n-pentane, iso-pentane, neo-pentane, n-hexane, ethers, diethyl ether, hydroxylated solvents, dextrose, aqueous saline, water, purified water, water for injection, diethylene glycol ethyl ether, isopropylidene glycerol, glycerol, N-methylpyrrolidone, N-pyrrolidone, methylethylketone, 1-dodecylazacycloheptane, dipropyleneglycol methyl ether, methyl acetate, ethyl lactate, dimethylformamide, N,N-diethyl-m-toluamide, ethylacetamide, caprolactam, decylmethylsulfoxide, triacetin and mixtures thereof. Typically, water with the qualification "for injections", as defined in acknowledged Pharmacopoeias, is used. In an embodiment, the solvent according to the present invention is present in an amount of about 99.99% or less, e.g. 90% or less, 80% or less, 70% or less, 60% or less, 50% or less, 40% or less, 30% or less, 20% or less, 10% or less.

Various diluent(s) or carrier(s) include, but are not limited to, mannitol, glycine, lactose, sucrose, trehalose, dextran, hydroxyethyl starch, gelatin, and the like. The amount of diluents may range from about 0.01% to about 95% of the composition. In an embodiment, the diluent according to the present invention is present in an amount of about 90% or less, e.g. 80% or less, 70% or less, 60% or less, 50% or less, 40% or less, 30% or less, 20% or less, 10% or less, 5% or less, 2.5% or less, 2% or less.

Various useful pH stabilizer(s) or pH adjusting agent(s) or buffer(s) include, but are not limited to, inorganic acids, organic acids, inorganic bases, and organic bases, acetic acid/acetate, sodium acetate, ascorbic acid, sodium ascorbate, sodium ethoxide, gluconate buffer, sodium carbonate, sodium hydroxide, potassium hydroxide, disodium hydrogen phosphate anhydrous, sodium dihydrogen phosphate monohydrate, magnesium carbonate, calcium carbonate, magnesium oxide, ammonia, hydrochloric acid, malic acid/malate, citric acid/citrate, sulfuric acid, nitric acid, phosphoric acid/phosphate, adipic acid, benzoic acid, sodium benzoate, boric acid, potassium phosphate, sodium acetate, sodium bicarbonate, tris buffer, sodium borate, glycine/glycimate, maleic acid, monobasic sodium phosphate, sodium phosphate monobasic monohydrate, sodium phosphate dibasic anhydrous, sodium diphosphate, glacial acetic acid, HEPES, lactic acid/lactate, tartaric acid/tartrate, fumaric acid, potassium metaphosphate, sodium tartrate, sodium citrate, dihydrate and combination thereof. Other buffering agents also include citric acid/phosphate mixture, acetate, barbital, Britton-robinson, cacodylate, collidine, formate, maleate, mclvaine, glutamic acid/glutamate, prideauxward, succinate, citrate-phosphate-borate (Teorell-Stanhagen), veronal acetate, MES (2-(N-morpholino) ethanesulfonic acid), Bis-Tris (bis (2-Hydroxyethyl) iminotris (hydroxymethyl) methane), ADA (N-(2-acetamido)-2-iminodiacetic acid), ACES (N-(carbamoylmethyl)-2-aminoethanesulfonic acid), PIPES (piperazine-N, N'-bis (2-ethanesulfonic acid)), MOPSO (3-(N-Morpholino)-2-hydroxypropanesulfonic acid), bistris propane (1,3-bis (tris (hydroxymethyl) methylamino) propane), BES (N, N-bis (2-hydroxyethyl)-2-aminoethane Sulfonic acid), MOPS (3-(N-morpholino) propanesulfonic acid), TES (N-tris (hydroxymethyl) methyl-2-aminoethanesulfonic acid), HEPES (N-(2-hydroxyethyl) piperazine-N'-(2-ethanesulfonic acid), dipso (3-(N, N-bis (2-hydroxyethyl) amino)-2-hydroxypropanesulfonic acid), MOBS (4-(N-morpholino)-butanesulfonic acid), tricine (N-tris (hydroxymethyl)) Methylglycine), GLY-GLY (glycylglycine), bicine (N, N-bis (2-hydroxyethyl) glycine), HEPBS (N-(2-hydroxyethyl) piperazine-N'-(4-butanesulfone) Acid)), TAPS (N-tris (hydroxymethyl) methyl)-3-amino-propanesulfonic acid), AMPD (2-amino-2-methyl-1,3-propanediol), Tapso (3-(N-tris (hydroxymethyl) methylamino)-2-hydroxy Propanesulfonic acid), Trizma™ (Tris (hydroxymethylaminomethane), Heppso (N-(2-hydroxyethyl) piperazine-N'-(2-hydroxypropanesulfonic acid), popso (piperazine-N, N')-Bis (2-hydroxypropanesulfonic acid)), TEA (triethanolamine), EPPS (N-(2-hydroxyethyl) piperazine-N'-(3-propanesulfonic acid), alone or in combination thereof. In an embodiment, the pH stabilizer according to the present invention is present in an amount of about 80% or less, e.g. 50% or less, 30% or less, 20% or less, 10% or less, 5%, or less.

Various useful tonicity adjusting agent(s) include, but are not limited to, potassium chloride, mannitol, glycerin, lactose, glycerol, dextrose, sodium chloride, sodium sulfate, sorbitol, trehalose, ammonium carbonate, ammonium chloride, ammonium lactate, ammonium nitrate, ammonium phosphate, ammonium sulfate, ascorbic acid, bismuth sodium tartrate, boric acid, calcium chloride, disodium calcium edetate, calcium gluconate, calcium lactate, citric acid, diethanolamine, dimethyl sulfoxide, disodium edetate, trisodium edetate monohydrate, sodium fluorescein, fructose, galactose, glycerin, lactic acid, lactose, magnesium chloride, magnesium sulfate, polyethylene glycol, potassium acetate, potassium chlorate, potassium chloride, potassium iodide, potassium nitrate, potassium phosphate, potassium sulfate, propylene glycol, silver acid, sodium acetate, sodium bicarbonate, sodium biphosphate, sodium bisulfite, sodium borate, sodium bromide, sodium cacodylate, sodium carbonate, sodium chloride, sodium citrate, sodium iodide, sodium lactate, metabisulfate sodium sulfite, sodium nitrate, sodium nitrite, sodium phosphate, sodium propionate, sodium succinate, sodium sulfite, sodium tartrate, sodium thiosulfate, sorbitol, maltose, sucrose, tartaric acid, triethanolamine, urea, urethane, uridine zinc sulfate, zinc chloride, albumin, amino acid aloneor, ringer's solution and lactated ringer's solution or any combination thereof. In an embodiment, the tonicity adjusting agent according to the present invention is present in an amount of about 60% or less, e.g. 30% or less, 20% or less, 10% or less, 5% or less.

Various useful preservative(s) include, but are not limited to, ethanol, parabens (methylparaben and/or propylparaben), benzalkonium chloride, benzethonium chloride, methyl, ethyl, propyl, and butyl esters of hydrobenzoic acid, benzoic acid, imidura, benzyl alcohol, bronopol, butylparaben, cetrimide, chlorhexidine, chlorobutanol, chlorocresol, cresol, ethylparaben, imidurea, phenoxyethanol, phenylethyl alcohol, phenylmercuric acetate, phenylmercuric borate, phenylmercuric nitrate, potassium sorbate, sodium benzoate, sodium propionate, sorbic acid, thimerosal, m-cresol, phenol, phenylmercuric salts, butylated hydroxyltoluene (BHT), butylated hydroxyanisole (BHA), propyl gallate, tocopherols, DMDM Hydantoin®, Euxyl® K400, Bronopol® (2-bromo-2-nitropropane-1,3-diol), chlorhexidine, 2-phenoxyethanol, chlorbutol, thiomersal and the like and mixtures thereof. In an embodiment, the preservative according to the present invention is present in an amount of about 20% or less, e.g. 10% or less, 5% or less, 2.5% or less.

Various useful antioxidant(s) include, but are not limited to, ascorbic acid and its salts, butylated hydroxytoluene, butylated hydroxyanisole, metal chelators such as ethylenediaminetetraacetic acid, ascorbyl palmitate, benzoic acid, benzyl alcohol, tocopherol, vitamin E, alpha-tocopherol, ascorbyl palmitate, sodium metabisulfite, sodium bisulphite, propyl gallate, n-propyl gallate, methionine, fumaric acid, malic acid, sodium ascorbate, BHA (butylated hydroxyanisole), BHT (butylated hydroxytoluene), citric acid, monothioglycerol, tert-butyl hydroquinone (TBHQ), phenols, myristyl-gamma-piccolinium chloride, phenylmer curic acetate and the like and mixtures thereof. In an embodiment, the antioxidant according to the present invention is present in an amount of about 20% or less, e.g. 10% or less, 5% or less, 2.5% or less.

Various useful wetting agent(s) or surfactant(s) or solubility enhancer(s) or permeation enhancer(s) include, but are not limited to, one or more of anionic, cationic, non-ionic, or zwitterionic surfactants or mixtures thereof such as sodium lauryl sulphate, polysorbate (e.g. polysorbate 20, polysorbate 40, polysorbate 60, and polysorbate 80), cetrimide, cetyl alcohol, stearyl alcohol, cetyl stearyl alcohol, cholesterol, polyethylene glycols, polyglycerin fatty acid esters such as decaglyceryl monolaurate and decaglyceryl monomyristate, sorbitan fatty acid esters such as sorbitan monostearate, polyoxyethylene sorbitan fatty acid esters such as polyoxyethylene sorbitan monooleate, polyoxyethylene alkyl ether such as polyoxyethylene lauryl ether, polyoxyethylene castor oil, polyoxyethylene polyoxypropylene block copolymers such as poloxamer (such as poloxamer 124, poloxamer 188, poloxamer 237, poloxamer 338, and poloxamer 407), and combinations thereof. The amount of wetting agent or surfactant or solubility enhancer or permeation enhancer according to the present invention ranges from about 0 to about 50% by weight of the composition. In an embodiment, the wetting agent according to the present invention is present in an amount of about 50% or less, e.g. 40% or less, 30% or less, 20% or less, 10% or less, 5% or less, or 2% or less.

The invention is further defined by reference to the following examples described in detail. It will be apparent to those skilled in the art that many modifications, both to materials and methods, may be practiced without departing from the scope of the invention. The following examples are provided to illustrate embodiments of the disclosure but they are by no means intended to limit its scope.

Mirabegron injection compositions were prepared by using quantitative formula as given in Table 1 and Table 2 under sterile conditions as per processes as mentioned in the present invention and were filled into a suitable container.

TABLE 1

Example - 1-2

| | Quantity (%) w/w | |
|---|---|---|
| Ingredients | 1 | 2 |
| Drug | 0.001-80 | 0.001-80 |
| pH adjusting agents | 0.001-60 | 0.001-40 |
| Wetting agents | 0-30 | 0.001-20 |
| Tonicity adjusting agents | 0-30 | 0.001-20 |
| Preservative | 0-20 | — |
| Antioxidant | 0-20 | — |
| Solvent | q.s. | q.s. |

In developing the parenteral formulation of mirabegron, the present inventors conducted extensive research and experiments. The solubility of API was studied in various solvent systems. For formulating immediate release injectable formulations, the solubility of the drug plays an important role as the final parenteral formulation has to be essentially a clear solution. The present inventors found that the API is practically insoluble in water. The present inventor surprisingly found that the API is found soluble when the pH is adjusted to the acidic side such as pH close to 3.0. The API solubility was found to increase from about 0.1 mg/mL to up to 100 mg/mL. While other techniques such as the use of co-solvent (such as propylene glycol) with or without heating failed to achieve desired drug solubility required for the successful development of immediate-release injectable formulations. Further, the inventors of the present invention were able to achieve maximum API solubility based on series of saturation solubility studies performed. The present inventors surprisingly found that maximum solubility of API was found in Acetate buffer having pH 4.5. The assessment of the successful development and stability of the solutions has been made on basis of the appearance of the solutions, the pH-value, osmolality, impurities content, and stability. The prepared formulations were found acceptable on these parameters.

TABLE 2

Example - 3-12

| | Quantity (%) w/w | | | | | | | | | |
|---|---|---|---|---|---|---|---|---|---|---|
| Ingredients | 3 | 4 | 5 | 6 | 7 | 8 | 9 | 10 | 11 | 12 |
| Mirabegron | 0.001-90 | 0.001-30 | 1 | 1 | 5 | 1 | 10 | 5 | 5 | 5 |
| Sodium acetate | 0-20 | 0-5 | — | — | 0.5 | 0.5 | 0.5 | 0.5 | 0.5 | 0.5 |
| Sodium phosphate monobasic | 0-20 | 0-5 | — | 0.38 | — | — | — | — | — | — |
| Sodium phosphate dibasic | 0-20 | 0-5 | — | 0.66 | — | — | — | — | — | — |
| Citric acid | 0-20 | 0-5 | 0.22 | — | — | — | — | — | — | — |
| Sodium citrate | 0-20 | 0-5 | 0.21 | — | — | — | — | — | — | — |
| Polysorbate-80 | 0-20 | 0-5 | — | — | — | — | — | 0.5 | 0.1 | 0.2 |
| Glacial acetic acid | 0-20 | q.s. | — | — | q.s. | q.s. | q.s. | q.s. | q.s. | q.s. |
| Hydrochloric acid | 0-20 | — | q.s. | q.s. | — | — | — | — | — | — |
| Water For Injection | 0-90 | q.s. | q.s. | q.s. | q.s. | q.s. | q.s. | q.s. | q.s. | q.s. |

Procedure: a) suitable vehicle (such as water for injection) was collected in a suitable container; b) the vehicle of step a) was cooled to a suitable temperature range (such as 20 to 25° C.); c) suitable excipients (such as a wetting agent, tonicity adjusting agent) was added with stirring for a suitable time to produce a clear solution; d) drug was added to the solution of step c) with stirring for a suitable time; e) the solution of step d) was stirred for a suitable time and the pH was adjusted using one or more suitable pH adjusting agents; f) the volume was made up to final batch size using water for injection; g) the solution of step f) was filtrated using suitable filters (such as 0.2-micron size); h) the solution of step g) was filled in appropriate size vials; i) the vials were stoppered using rubber stoppers; j) the vials were capped using suitable seals (such as aluminum flip-off seals).

TABLE 3

Results

| Example No. | Appearance | pH | Assay |
|---|---|---|---|
| 5 | Clear | 3.61-3.68 | 99.3 |
| 6 | Solution | 3.57-3.58 | 100.1 |
| 7 | | 5.03-5.03 | 102.1 |
| 8 | | 5.05-5.05 | 103.8 |
| 9 | | 5.01-4.97 | 96.6 |
| 10 | | 5.1-5.13 | 101.3 |
| 11 | | 5.02-5.04 | 102.6 |
| 12 | | 4.67-4.73 | 101.6 |

Example 13

The injection formulations were evaluated to determine the effect of mirabegron in animals such as C57BL/6 mice etc. The purpose of this study was to determine the effect of mirabegron on modulation in biomarkers such as uncoupling protein 1 (UCP1), Peroxisome proliferator-activated receptor-gamma coactivator-1alpha (PGC-1α) and others in this category to check pharmacokinetics after single and multiple localized microinjections in iWAT (Inguinal white adipose tissue). Mirabegron at a dose up to 1 mg per animal has shown a statistically significant increase in expression of biomarkers in iWAT which clearly indicated that mirabegron is causing marked thermogenesis after localized microinjections.

What is claimed:

1. A pharmaceutical composition suitable for parenteral administration in the form of an aqueous solution comprising:
    a) about 0.001% to about 20% of mirabegron, wherein the mirabegron is in solution in the composition;
    b) about 0.01% to about 20% of one or more pH adjusting agents selected from the group consisting of sodium phosphate, citric acid, sodium citrate, glacial acetic acid and hydrochloric acid;
    c) about 0.01% to about 20% of one or more wetting agents selected from the group consisting of sodium lauryl sulphate, polysorbate, and poloxamer; and
    d) water as a parenteral solvent;
wherein the pH of the composition is about 3.5 to about 5.5, the osmolality is about 100 to about 400 mOsm/kg, a weight ratio of mirabegron to wetting agent is about 1:0.001 to 1:0.5, and the composition consists of a single phase.

2. The composition according to claim 1, wherein the composition further comprises one or more pharmaceutically acceptable excipients selected from the group consisting of, permeation enhancers, tonicity adjusting agents, diluents, suspending agents, complexing agents, preservatives, antioxidants, and combination thereof.

3. The composition according to claim 2, wherein the tonicity adjusting agent is selected from the group consisting of, sodium acetate, sodium chloride, dextrose, sodium lactate, calcium chloride, sodium bicarbonate, and potassium chloride.

4. A process for preparing the liquid mirabegron injection pharmaceutical composition according to claim 1, which comprises: dissolving one or more pharmaceutically acceptable excipients such as wetting agent, pH adjusting agents, and mirabegron in water as a parenteral solvent to form a liquid composition.

5. The process according to claim 4, comprising the step of terminal sterilization or aseptic filtration.

6. The process according to claim 5, comprises filtrating said composition and filling it into glass vials.

7. A sterile, immediate release pharmaceutical composition suitable for parenteral administration in the form of an aqueous solution consisting of:
    a) about 1% to about 10% w/w of mirabegron in solution in the composition,
    b) 0 to about 1.04% w/w of one or more first pH adjusting agents selected from the group consisting of sodium phosphate, citric acid and sodium citrate, and an amount of a second pH adjusting agent selected from glacial acetic acid and hydrochloric acid, wherein the amount of the first pH adjusting agent if present and the amount of the second pH adjusting agent are sufficient to provide a pH of the solution of about 3.5 to about 5.1,
    c) optionally about 0.1% to about 0.5% w/w of polysorbate, wherein a weight ratio of the mirabegron to the optional polysorbate when present is about 1:0.01 to 1:0.5,
    d) optionally about 0.5% w/w of sodium acetate, and
    e) water as a parenteral solvent,
wherein the pH of the composition is about 3.5 to about 5.1.

8. The pharmaceutical composition of claim 7, wherein the composition consists of about 5% w/w of mirabegron, about 0.5% w/w of sodium acetate, about 0.1% to about 0.5% w/w polysorbate, glacial acetic acid, and water.

9. The pharmaceutical composition of claim 7, wherein the composition consists of about 1% to about 10% w/w of mirabegron, about 0.5% w/w of sodium acetate, glacial acetic acid, and water.

10. The pharmaceutical composition of claim 7, wherein the composition consists of about 1% w/w of mirabegron, about 1% w/w of sodium phosphate, hydrochloric acid, and water.

11. The pharmaceutical composition of claim 7, wherein the composition consists of about 1% w/w of mirabegron, about 0.22% w/w of citric acid, about 0.21% w/w of sodium citrate, hydrochloric acid, and water.

12. A sterile immediate release pharmaceutical composition suitable for parenteral administration consisting of:
    (a) about 0.001% to about 10% of mirabegron, wherein the mirabegron is present in the composition at a concentration of from about 1 mg/ml to about 50 mg/mL and is dissolved in the composition;
    (b) about 0.01% to about 5% of one or more pH adjusting agents selected from the group consisting of sodium phosphate, citric acid, sodium citrate, glacial acetic acid, and hydrochloric acid, and being present in an amount to provide a pH of the composition in the range of about 3.5 to about 5.5;
    (c) about 0.001% to about 1% of one or more wetting agents selected from the group consisting of sodium lauryl sulphate, polysorbate, and poloxamer;
    (d) about 0.001% to about 2% of one or more tonicity adjusting agents selected from the group consisting of sodium acetate, dextrose, sodium lactate, calcium chloride, sodium bicarbonate, and potassium chloride present in an amount to provide an osmolality of from about 100 to about 400 mOsm/kg; and
    (e) water as a parenteral solvent,
wherein the weight ratio of mirabegron to wetting agent is about 1:0.01 to 1:0.5.

13. The composition according to claim 12, wherein the composition consists of:
    about 1-10% mirabegron;
    about 0.01-0.5% sodium acetate;
    about 0.01-0.5% polysorbate 80;
    glacial acetic acid, and
    water for injection.

14. The composition according to claim 12, wherein the composition consists of:
    about 10 mg/ml to about 50 mg/mL mirabegron;
    about 0.01 to 5 mg/mL sodium acetate;
    about 0.01 to 5 mg/mL polysorbate 80;
    glacial acetic acid, and
    water for injection.

* * * * *